(12) United States Patent
Roloff et al.

(10) Patent No.: US 12,191,022 B2
(45) Date of Patent: Jan. 7, 2025

(54) WELLNESS PROGRAM NAVIGATION ENGINE

(71) Applicant: Integer Health Technologies, LLC, Arlington, TX (US)

(72) Inventors: Scott Roloff, Arlington, TX (US); Ken Grifno, The Colony, TX (US); Jack McCallum, Benbrook, TX (US); William McCallum, Fort Worth, TX (US)

(73) Assignee: Integer Health Technologies, LLC, Arlington, TX (US)

( * ) Notice: Subject to any disclaimer, the term of this patent is extended or adjusted under 35 U.S.C. 154(b) by 229 days.

(21) Appl. No.: 17/855,694

(22) Filed: Jun. 30, 2022

(65) Prior Publication Data
US 2024/0006046 A1    Jan. 4, 2024

(51) Int. Cl.
*G16H 20/30* (2018.01)
*G06Q 10/06* (2023.01)

(52) U.S. Cl.
CPC .................. *G16H 20/30* (2018.01)

(58) Field of Classification Search
CPC ........ G16H 20/30; G16H 15/00; G16H 40/20; G16H 20/00; G16H 50/30
See application file for complete search history.

(56) References Cited

U.S. PATENT DOCUMENTS 8,239,246 B1 * 8/2012 Bigham ................. G06Q 40/08
                                                                 705/7.38
2016/0275431 A1 * 9/2016 Gouvernel ....... G06Q 10/06393

* cited by examiner

*Primary Examiner* — Maroun P Kanaan
(74) *Attorney, Agent, or Firm* — Vincent J. Allen; James H. Ortega; Carstens, Allen & Gourley, LLP (57) ABSTRACT

A method and/or system that is a navigation engine with a visual interface that evaluates wellness programs based on their effect on the participants' healthcare costs and absences from work, and then calculates the programs' ROIs (Returns on Investment). The engine can also generate a list of employees and/or other individuals who could benefit from a wellness program but who are not participating, and the impact on the healthcare costs, medically-related absence costs and ROI if they did. In addition, the engine can recommend wellness and safety programs that have not been implemented, but should be, along with the impact such programs could have on the medical and pharmacy claims and medically-related absences.

6 Claims, 4 Drawing Sheets

Occupational Outcome—Level 1

WELLNESS PROGRAM NAVIGATION ENGINE

TECHNICAL FIELD

A method and/or system consisting of a navigation engine for wellness programs that evaluates participant outcomes and determines a program's occupational outcome, healthcare outcome and Return on Investment (ROI).

BACKGROUND

Healthcare is a significant expenditure for employers, insurers and individuals.

In addition, medically-related absences from work are a significant cost to employers and employees.

Wellness programs are a way to decrease healthcare expenditures and medically-related absences.

These programs aim to make their participants healthier because healthier individuals consume less healthcare and are sick less often, missing fewer days of work.

The types of wellness programs include: (1) general wellness programs for everyone, such as walking and weight watchers programs, (2) disease management programs for individuals with specific chronic conditions, such as diabetes and obesity, and (3) Employee Assistance Programs (EAPs) for individuals with behavioral health issues.

When an employer sponsors a wellness program the participants may include employees, the dependents under the employer's health plan, and retirees and their dependents when the employer provides retiree health benefits.

Employers and others sponsoring wellness programs know what they pay vendors for them (or if they create their own programs, what they cost to create and operate them). They have no idea what they get in return.

Vendors may measure certain qualitative factors to demonstrate that their programs are working, such as the number of steps taken in a walking program or the decrease in participant A1c scores in a diabetes management program.

These qualitative measures may, or may not, be reasonable proxies for the program's effect on the only quantitative thing that matters—the participants' healthcare costs and medically-related absences.

What is needed is a way to quantify the effect of a wellness program on the participants' healthcare costs and medically-related absences so that the sponsor can determine if the program is working—or not, and if it isn't working, what to do about it.

That is what the navigation engine does; evaluates a wellness program based on its occupational outcome, healthcare outcome and ROI.

SUMMARY

A method and/or system consisting of a navigation engine that evaluates wellness programs based on their effect on the participants' healthcare costs and medically-related absences from work.

The navigation engine begins with a visual interface that displays all the engine's analytics and data on the computer monitor at one time, arranging such items in categories and subcategories represented by circles or other images for quick retrieval by hoovering the computer mouse's cursor over the circle with the desired item and clicking on it.

The navigation engine intakes employer Human Resources (HR) data and combines it with a wellness program's enrollment and costs to determine the program's "occupational outcome," the program's impact on employee absences from work.

For EAPs, the occupational outcome includes an analysis of participating employees whose employment was terminated, either voluntarily or involuntarily.

The navigation engine can then determine a wellness program's "healthcare outcome" and ROI by intaking the medical and pharmacy claims under the health plan and combining them with the HR and program data. In addition, the engine may intake the medical and pharmacy claims under the workers' compensation program too.

The navigation engine can generate a list of employees and/or other individuals that could benefit from the wellness program but who are not participating, and the impact on the program's healthcare outcome and ROI if those employees or individuals did participate.

The navigation engine can also recommend wellness and safety programs that the employer has not implemented, but should, along with the impact such programs could have on the medical and pharmacy claims and medically-related absences.

BRIEF DESCRIPTION OF THE DRAWINGS

A complete understanding of the navigation engine may be obtained by referring to the accompanying drawings in conjunction with the following detailed description.

DETAILED DESCRIPTION

Various objects, features, aspects and advantages will become apparent from the following detailed description and accompanying drawings. The principles are described with specificity. This description and the drawings, however, are not intended to limit the scope of the principles disclosed herein. These principles might also be embodied in other ways and include different steps or combinations of steps similar to those described.

A method and/or system that is a navigation engine that evaluates wellness programs based on their effect on the participants' healthcare costs and absences from work.

Figure 1:
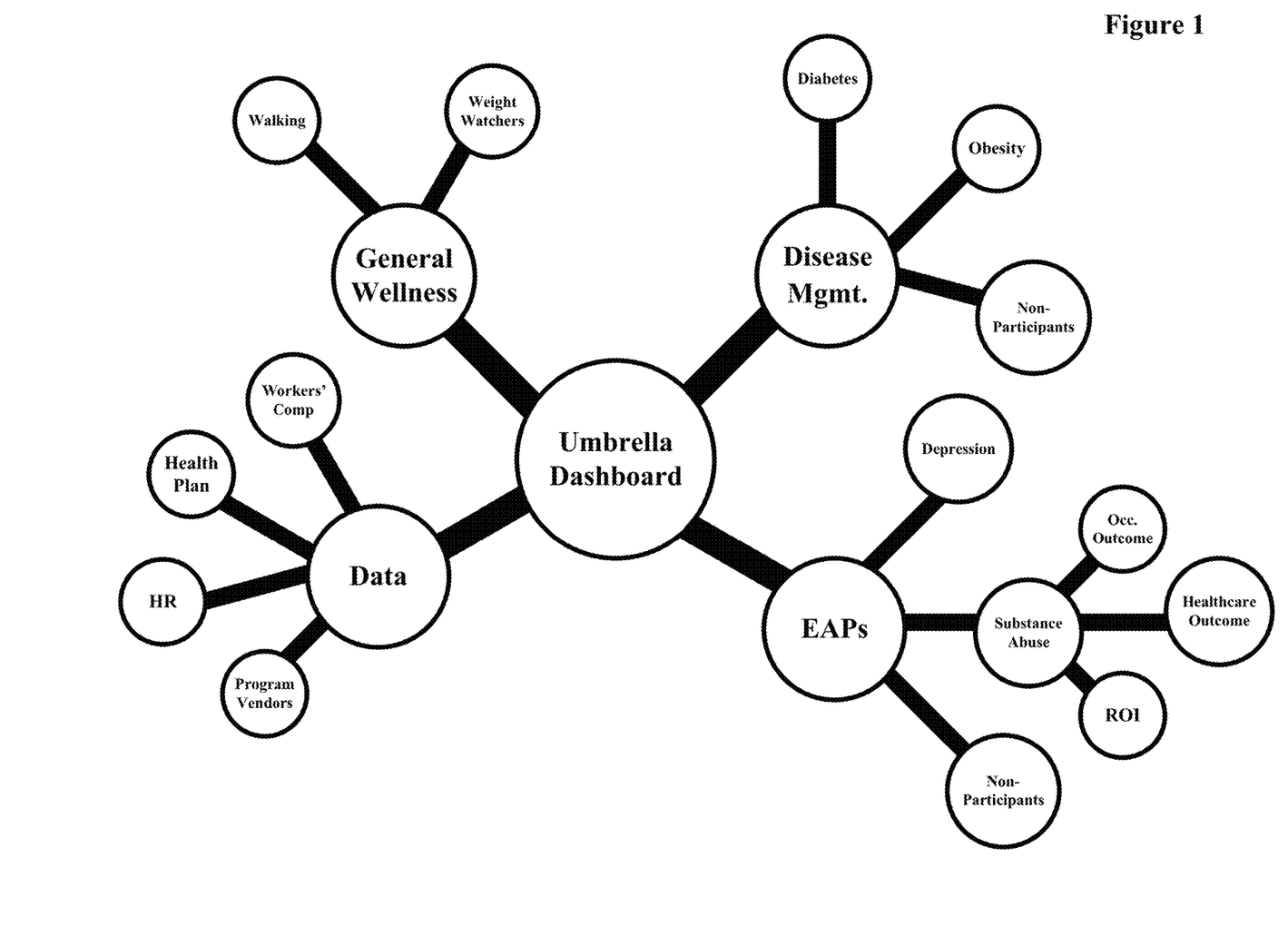
FIG. 1 shows how the navigation engine visually displays all the data on the computer monitor at one time, arranging the data into categories and subcategories for easy retrieval by hoovering the computer mouse's cursor over the desired data and clicking on it.

The navigation engine is deployed on a computer connected to a monitor and mouse. As shown in FIG. 1, the engine employs the novel approach of representing categories and subcategories (and sub-subcategories, etc.) of material with functionally labeled circles or other images connected by stems in a hierarchical organization on a single computer screen. Descending circles in the hierarchy represent more detailed subsets of material. Hovering the computer mouse's cursor over a circle displays thumbnails of the dashboards and reports available under it. For example, major categories may be the general wellness programs, disease management programs, EAPs and the data input into the engine. Subcategories may be the specific programs deployed under each category, such as walking and weight watchers programs under the general wellness program category, diabetes and obesity programs under the disease management category, and depression and substance abuse programs under the EAP category. A sub-subcategory may be the occupational outcome, healthcare outcome and ROI under each specific program.

The circle for each wellness program may be linked to the navigation engine's determination of the program's ROI so that such circles may be color coded to indicate the program's success or failure. For example, the circles for programs meeting or exceeding their targeted ROI may be colored green, the circles for programs not meeting their targeted ROI but with an ROI of 0% or more may be colored yellow, and the circles for programs with a negative ROI may be colored red. The shade of the color may also be darker or lighter based on where the ROI falls within the color's range (e.g., a dark green for a program significantly surpassing its target ROI, while a light green for a program just meeting its target).

The user can click on a circle with the computer mouse to open that category, or click on a thumbnail to access a dashboard or report directly.

The dashboards and reports are interactive and permit filtering the results by various metrics and/or combinations thereof, including programs, periods, business units and/or departments, job descriptions and/or functions, and employer locations and/or geographies. When medical and pharmacy claims are input into the navigation engine additional filters may include employees versus dependents, risk scores, social determinants of health (SDOH), job demographics, and health plan/clinical data, including the type of health plan covering the person.

The dashboards and reports may also contain relative qualitative measures of a wellness program's success, including employee turnover rates, average annual primary care physician (PCP) visits, annual health risk assessment results, and program specific measures such as the steps walked in a walking program, the pounds lost in a weight watchers program, and the decreases in A1c scores in a diabetes program.

This navigation technology improves the computer's functionality by transforming the literal display of data into a visual one on a single computer screen; thereby improving computer and network performance by decreasing the resources used to open and close screens while searching for the right one, while increasing the effectiveness and speed of the user's search process.

Figure 2:
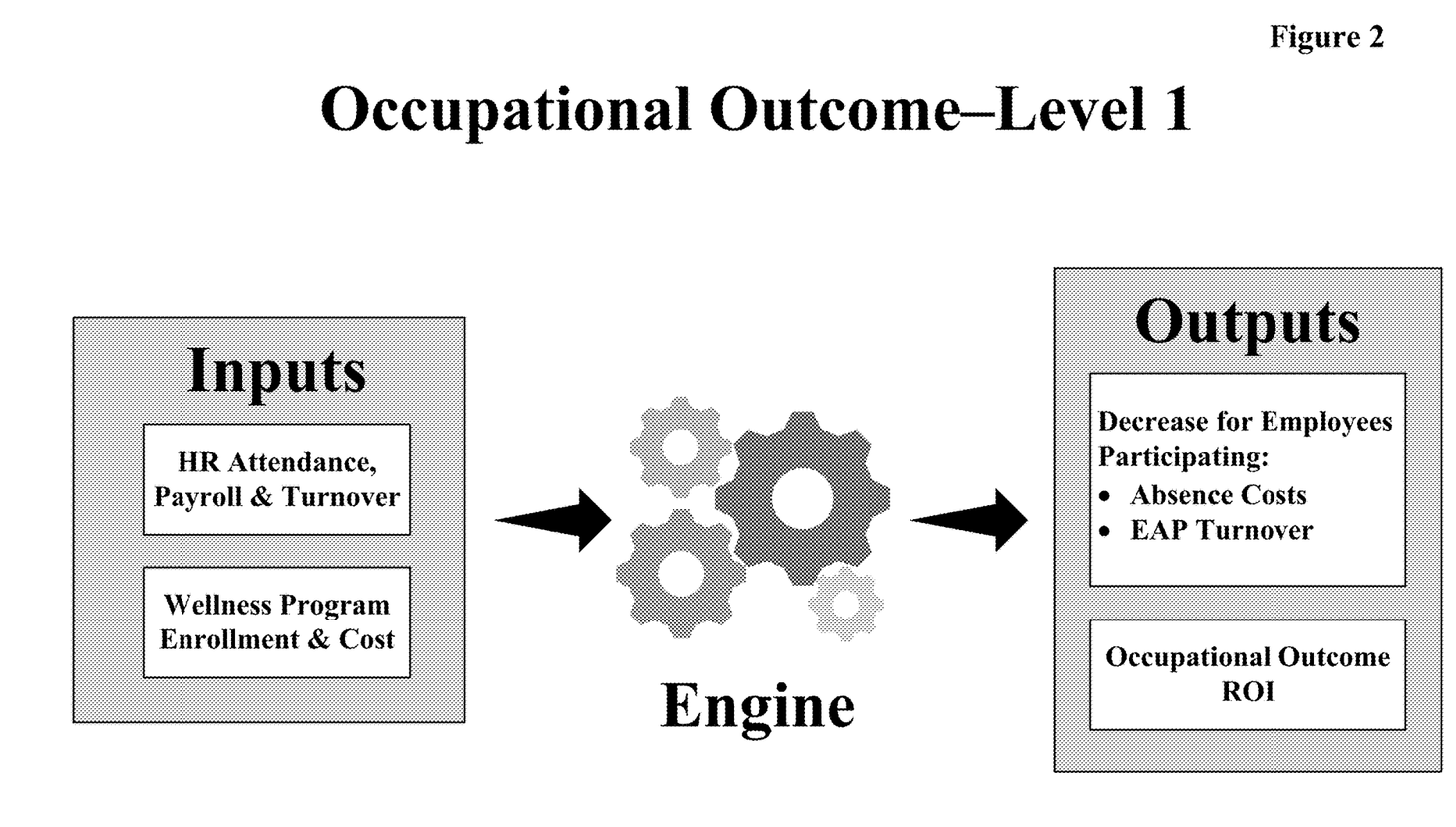
FIG. 2 shows an overview of the inputs into the navigation engine and the resulting outputs at the first level of program evaluation—the program's occupational outcome and respective ROI.

FIG. 2 shows the inputs into the navigation engine for the first level of evaluation of a wellness program—the program's occupational outcome—and the engine's outputs at that level. These inputs include: (1) HR data (e.g., time & attendance, payroll, and turnover), and (2) program data (e.g., enrollment and cost). This input data is arranged in databases, which are themselves arranged in tables with schemas (i.e., logical groupings) that permit the engine to extract the data and perform the engine's algorithms.

At the occupational outcome level, the navigation engine compares each participating employee's sick days during the wellness program year (or other period under evaluation) to that employee's sick days during the employee's base year. If an employer uses a PTO regime (Paid Time Off) instead of vacation and sick days, then the engine will use the PTO days instead. Sick and PTO days are collectively referred to as absence days below.

The base year is the year (or other period) immediately before the employee joins the program, so the base year will differ for each employee. If the employee joined the program in the first year that the employee became an employee, then the navigation engine creates a synthetic base year for the employee with the number of absence days equal to the average base year absence days for similarly situated employees as determined using the HR data set (e.g., age, gender, job description, location, and other job demographics).

For each participating employee, the engine subtracts the current year's absence days from that employee's base year's absence days; and then aggregates the results for all the participants.

A positive number indicates that the program may be working— absence days have decreased—while a negative number indicates that the program may not be working because absence days have increased.

The engine next values each participating employee's change in absence days at that employee's current year compensation rate (or a normalized rate for all participants); and then aggregates those results for all the participants.

The engine determines the program's occupational outcome ROI by comparing the overall value assigned to the change in absence days to the program's overall cost as follows: (1) the overall value of the change in absence days (may be positive or negative), less (2) the overall cost of the program (if the overall value of the change in absence days is positive, this will decrease that positive value, while if the overall change is negative it will increase it), with that difference divided by (3) the overall cost of the program.

For example, assume that Employee A participates in a wellness program for which the employer paid $350 per employee during the current year, Employee A's compensation in the current year is $100,000 (and there are 260 working days in the year), and Employee A missed 10 days of work in the base year, and 9 days in the current year. The ROI of the program vis-à-vis Employee A would be 9.9%, calculated as follows: (((10−9)×($100,000÷260))−350)÷350=9.9%.

When rolling up these items for all 100 employees participating in the wellness program the employer paid $35,000 for the program during the current year (100× $350=$35,000), these employees missed 1,100 days of work in their respective base years, and 950 in the current year, with the 150 day difference valued at $40,000 (calculated at the employee level based on the employee's current year compensation and then rolled up), producing a current year ROI for the program of 14.3%, calculated as follows: ($40,000−$35,000)÷$35,000=14.3%.

If the wellness program is an EAP, an additional consideration is that employees with behavioral health issues tend to terminate their employment, voluntarily or involuntarily, at a higher rate than employees without behavioral health issues. The navigation engine therefore tracks the number of employees participating in an EAP that terminate their employment during the year and assigns a savings amount to them of $0 (i.e., the value of the excess of the absence days during the base year over the value of the absence days during the current year), or alternatively, a negative amount based on the employer's turnover costs as discussed below.

The engine can then roll up the wellness program's ROIs for each year to produce an inception-to-date ROI by taking each year's numbers and increasing them for inflation from that year (or decreasing them for deflation). For example, assume that in Year 1 the program's overall numbers were $34,000 in savings and a program cost of $30,000, while in Year 2 those numbers were $40,000 in savings and $35,000 of program costs. The inflation rate from Year 1 to Year 2 was 5%. The inception-to-date ROI would be 13.8%, calculated as follows: ((($34,000×105%)+$40,000)−(($30,000×105%)+$35,000))÷(($30,000×105%)+$35,000) =13.8%.

Figure 3:
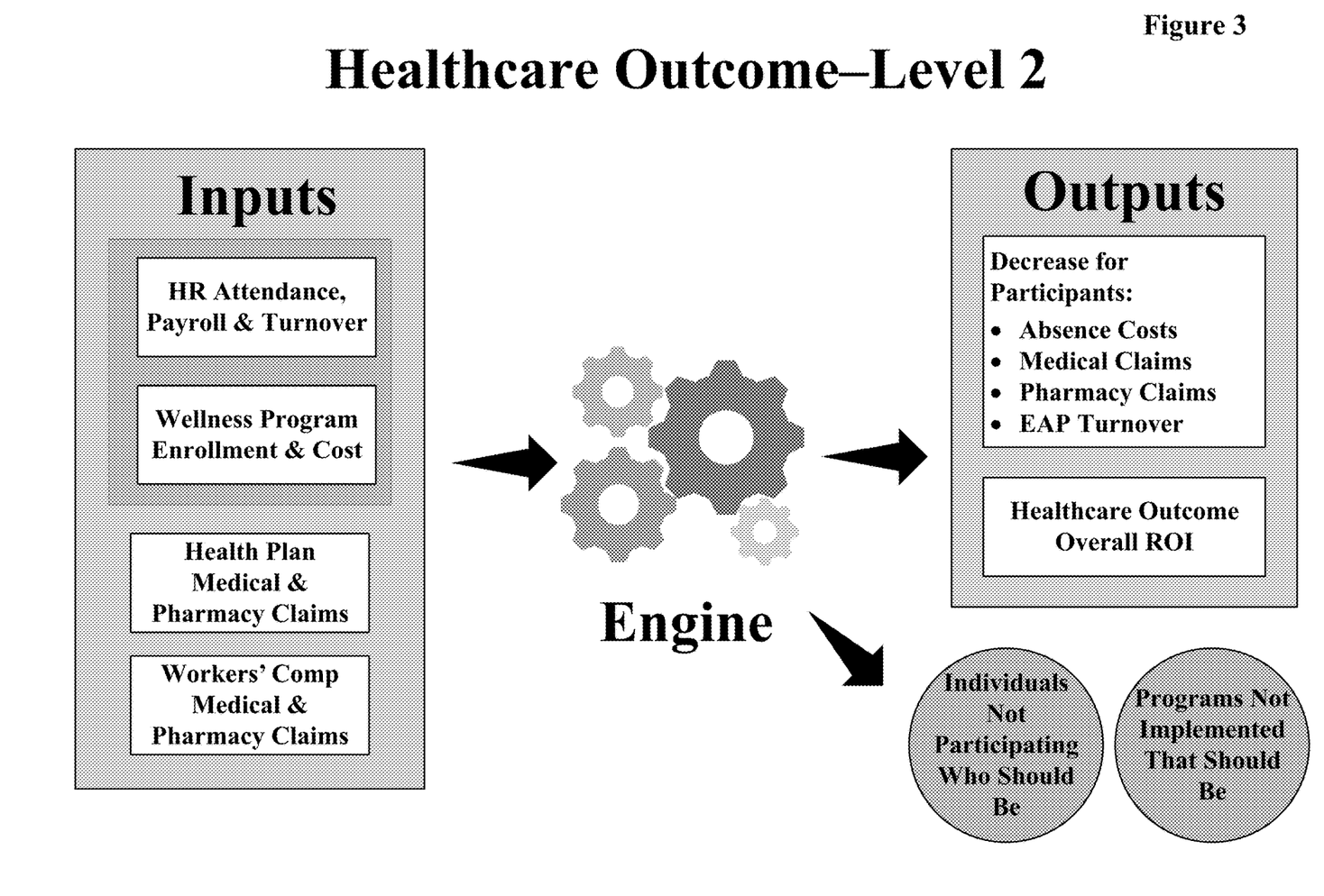
FIG. 3 shows an overview of the inputs into the navigation engine (the inputs from FIG. 2 plus additional items) and the resulting outputs at the second level of program evaluation—the program's healthcare outcome and overall ROI.

FIG. 3 shows the second level of evaluation of a wellness program— the program's healthcare outcome. This level compares a participant's inputs from the occupational outcome evaluation plus their medical and pharmacy claims under the health plan during their base year versus the current year (and for EAPs, the turnover costs). In addition, the inputs can include the medical and pharmacy claims under the workers' compensation program too. This input data is arranged in databases, which are themselves arranged in tables with schemas that permit the engine to extract the data and perform the engine's algorithms. Note that the occupational outcome measures only a program's effect on employees as an employer will not have any absence days on non-employee participants. In contrast, the healthcare outcome measures it on all program participants (both employees and non-employees) and in some cases the impact of individuals not participating in a program who could benefit from it, with the ability to segregate the results by these categories.

For the best results, the health plan claims should be the total allowed claims, which includes the employer/plan paid portion and the portion paid by the employees and/or patients through copays and deductibles. If the employee/patient paid portion is unavailable, however, the navigation engine can use just the employer/plan paid claims.

The navigation engine sorts through each patient's medical and pharmacy claims for the base year and the then current year and groups them together according to the root diagnosis (i.e., the condition or injury causing the claim) based upon the diagnosis, procedure and other codes used in the claims. For example, when grouping together claims for a root diagnosis of diabetes the engine would group under diabetes a PCP office visit to monitor the patient's diabetes, an emergency room visit for diabetic shock, and a prescription for insulin. The engine would not group under diabetes the claims related to the person's breaking their arm in a fall.

For employees, the navigation engine juxtaposes the dates of their medical and pharmacy claims for each root diagnosis against the employee's sick or PTO days to identify absence days related to the diagnosis. For example, if an employee has medical claims for a heart attack on Tuesday, the engine assumes that the employee's PTO day on Tuesday (and a specified number of following days) was because of the heart attack.

The engine values each employee's medically-related absence days at that employee's compensation rate during the respective year (or a normalized rate for all the employees for that year).

For individuals joining a program simultaneously with joining the health plan and/or employer, the navigation engine creates a synthetic base year based on the individual's risk score, medical and pharmacy claims, and medically-related absence costs contained in the individual's first year of data as compared to the base years of similar individuals participating in the program.

For example, suppose an employee joins a diabetes management program on their first day of work. The navigation engine may construct a synthetic base year for such employee based upon the average base year medical and pharmacy claims and medically-related absence costs of other employees with a similar risk score and comorbidities.

To calculate a risk score the navigation engine may use an open-source risk scoring system, such as HHS-HCC (Department of Health and Human Services-Hierarchical Condition Categories), CDPS (Chronic Illness & Disability Payment System), or CMS-HCC (Centers for Medicare & Medicaid Services-Hierarchical Condition Categories).

The engine may overlay the risk score with certain social determinants of health (SDOH), job demographics, and health plan/clinical data. SDOH include a person's ZIP code (which may indicate the person's access to healthy food) and compensation (which may indicate the person's ability to pay for healthcare). Job demographics include a person's job description (and from that, the physicality required by their position), position rank, tenure, and compensation (including hourly versus salary and part-time versus full-time). Health plan/clinical data include the type of health plan that the person has enrolled in (e.g., HMO—Health Maintenance Organization, PPO—Preferred Provider Organization or HDHP—High Deductible Health Plan) and clinical variables such as height, weight, and the results of any health assessments or evaluations.

Using the selected risk scoring system and any SDOH, job demographics and health plan/clinical data, the navigation engine analyzes the individual's HR data and medical and pharmacy claims to determine their risk score based on their age, gender, diagnoses, and drug prescriptions—the diagnoses and drug prescriptions revealing the person's comorbidities. The engine normalizes the risk scores so that individuals of average health receive a risk score of 1.000, individuals healthier than average a score below 1.000 (the lower the score, the healthier), and individuals sicker than average a score above 1.000 (the higher the score, the sicker). As described below, under certain circumstances the engine may further normalize the results by assigning an individual with a score below 1.000 a score of 1.000.

For each individual's base year or synthetic base year (and any years after the base year, but before the current year), the engine increases the claims and the value of the medically-related absence costs for inflation to the current year (or decreases them for deflation, as the case may be).

Figure 4:
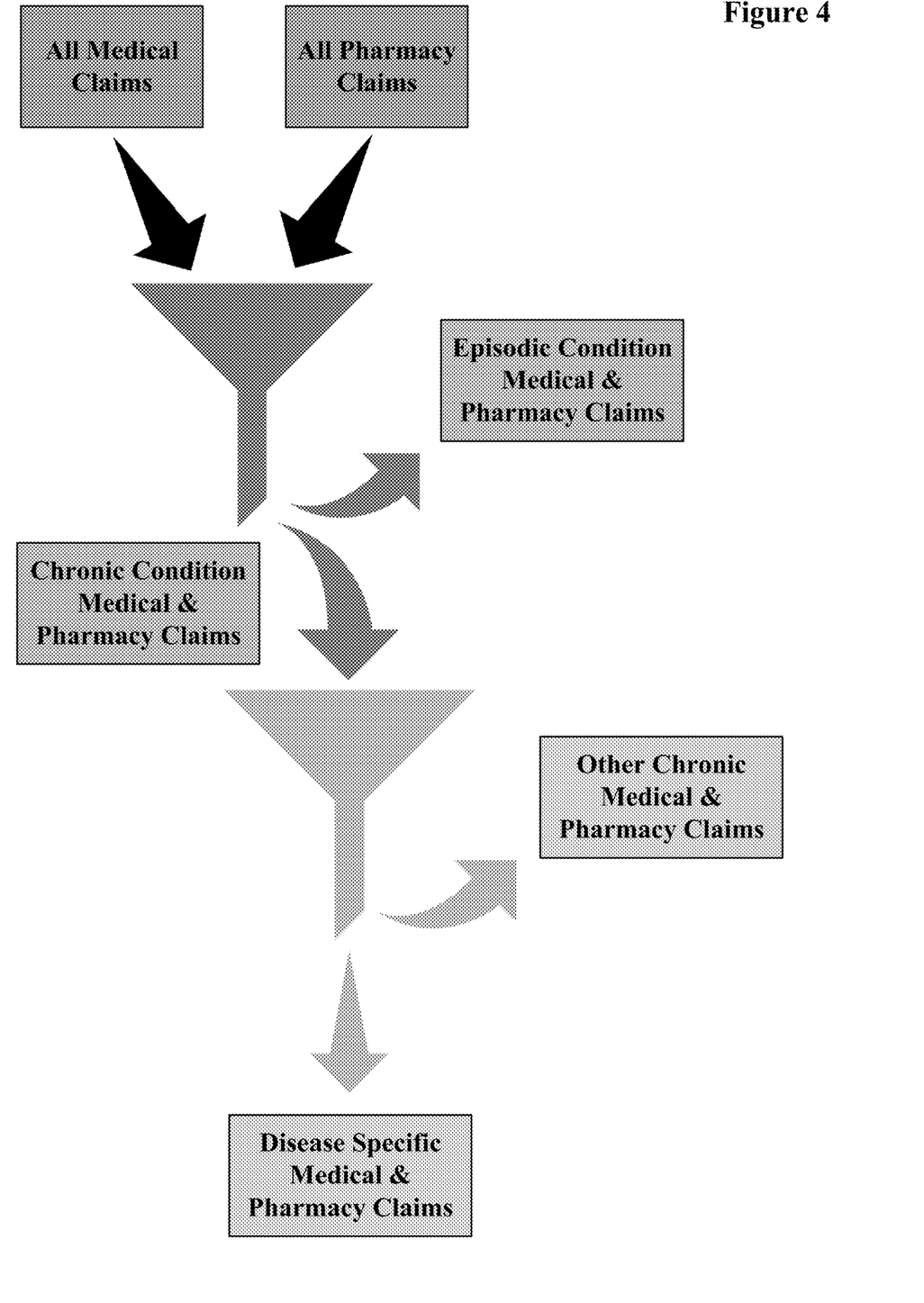
FIG. 4 shows the types of medical and pharmacy claims (and by implication, the respective medically-related absence costs) that may be used when evaluating a wellness program.

The navigation engine uses the claims and medically-related absence costs, with the program enrollment and cost data, to evaluate the program's healthcare outcome. As shown in FIG. 4, the user may select which claims (and by implication absence costs) to include/exclude when evaluating a particular program.

For a general wellness program the user may include all medical and pharmacy claims and medically-related absence costs in the evaluation, or only those concerning chronic conditions. There are two categories of root diagnoses: (1) diagnoses concerning episodic conditions that have a beginning and an end (e.g., a broken leg), and (2) diagnoses concerning chronic conditions that never or seldom go away (e.g., diabetes). Generally, workers' compensation programs deal with employee injuries, which will be episodic conditions.

For a disease management program the user may include all medical and pharmacy claims and medically-related absence costs in the evaluation, only those concerning chronic conditions (including behavioral health issues), or only those concerning the specific chronic condition that the program addresses.

For EAPs the user may include all medical and pharmacy claims and medically-related absence costs in the evaluation, only those concerning chronic conditions (including behavioral health issues), only those concerning behavioral health issues, or only those concerning the specific behavioral health issue that the program addresses.

For each participant the engine subtracts: (1) the current year costs of the respective medical and pharmacy claims and medically-related absence costs, from (2) their base year costs, as adjusted for inflation; and then aggregates the results for all the participants.

The engine calculates the program's healthcare outcome ROI by comparing the program's overall savings to the program's overall cost as follows: (1) the overall value of the change in medical and pharmacy claims and medically-related absence costs (may be positive or negative, a positive number when the costs have decreased, and a negative number when they have increased), less (2) the overall cost of the program (if the overall value of the change in claims and absence days is positive, this will decrease that positive value, while if the overall change is negative it will increase it), with the difference divided by (3) the overall cost of the program.

For example, assume that Employee B participates in a wellness program for which the employer paid $100 per employee in the current year, and the employer also gave each participating employee a $100 discount off their health insurance premiums. In the year before Employee B joined the program (i.e., the base year) Employee B had $6,500 in medical claims and $2,500 in pharmacy claims, and $1,000 in absence costs related to those claims, all as adjusted for inflation to state them in current year dollars. During the current year, Employee B had $6,400 in medical claims, $2,600 in pharmacy claims and $800 in absence costs. The ROI of the program vis-à-vis Employee B would be 0%, calculated as follows: (($6,500−$6,400)+($2,500−$2,600)+($1,000−$800)−$100−$100)÷($100+$100)=0%.

When rolling up these items for all 500 employees participating in the wellness program the employer paid $100,000 for the program in the current year (500×($100+$100)=$100,000), and the total changes from each participant's base year to the current year were a $50,000 decrease in medical claims, a $12,000 decrease in pharmacy claims, and a $40,000 decrease in the absence costs related to those claims, producing a current year ROI for the program of 2.0%, calculated as follows: ($50,000+$12,000+$40,000−$100,000)÷$100,000=2.0%.

The engine can then roll up the wellness program's ROIs for each year to produce an inception-to-date ROI by taking each year's unadjusted numbers and increasing them for inflation from that year (or decreasing them for deflation). For example, assume that in Year 1 the program's overall numbers were $1,850 in savings and a program cost of $92,500, while in Year 2 those numbers were $2,050 in savings and $110,000 of program costs. The inflation rate from Year 1 to Year 2 was 8%. The inception-to-date ROI would be 1.9%, calculated as follows: (($1,850×108%)+$2,050)÷(($92,500×108%)+$110,000)=1.9%.

As discussed above, employees with behavioral health issues tend to terminate their employment, voluntarily or involuntarily, at a higher rate than employees without behavioral health issues. When evaluating EAPs at the program level, turnover costs are therefore an additional item that can be included in the ROI calculation.

Turnover costs include: (1) severance payments, (2) payments for unused vacation time, (3) recruiting costs for the replacement, such as search firm fees and employment ads, and (4) payroll costs during the orientation and training period for the new employee replacing the terminated employee.

For example, assume that an employer has an EAP to combat depression. Sifting through the medical and pharmacy claims in the program's base year (i.e., the year before the employer started the program) identifies 75 employees with a depression diagnosis or who were on anti-depressants. During that year, 25 of these employees quit or were fired—a 33% turnover rate (25÷75=33%). During the current year there are 30 employees in the EAP. Based on the 33% turnover rate the expected turnover would be 10 (30×33%=10). The actual turnover was 6, cutting the turnover rate to 20% (6÷30=20%). If the employer's turnover cost is $15,000 per employee, the EAP saved an additional $60,000 ((10−6)×$15,000=$60,000). This $60,000 can be added to the program's savings when calculating the ROI.

The navigation engine also identifies individuals not participating in a disease management program or EAP who would benefit from it and calculates the impact on the program's savings and ROI if they participated.

The navigation engine does this by mapping the list of root diagnoses to the various disease management programs and EAPs.

The navigation engine also catalogs the root diagnoses in each patient's medical and pharmacy claims.

When a patient has a root diagnosis mapped to a program, the navigation engine determines if that individual is enrolled in that program. If not, the engine puts the person on the list of individuals not enrolled in the program who could benefit from it. This list may be represented by one of the subcategory circles under the navigation engine's circle for the program, with viewing restricted to only positions authorized to know an individual's healthcare condition, such as case managers.

For each individual on such a list for a program, the navigation engine determines the impact that such program could have on that person; and then rolls up those results to determine the overall impact on the program's healthcare outcome and ROI if all such individuals joined the program.

The navigation engine does so by first determining the average risk-adjusted per person benefit of the program as follows: (1) the average base year risk-adjusted medical and pharmacy claims, and medically-related absence costs, adjusted for inflation, of the individuals' participating in the program, less (2) their average current year risk-adjusted costs, with that difference divided by (3) their average base year risk-adjusted costs (adjusted for inflation), which yields the program's average risk-adjusted percentage decrease in costs. This percentage may be determined separately for employees and non-employees (as non-employees will not have any medically-related absence costs) with the employee percentage applied to non-participating employees and the non-employee percentage applied to non-employee non-participants. For these calculations, any individual with a risk score below 1.000 is assigned a risk score of 1.000, and the average risk-adjusted claims and absence costs are determined by dividing the unadjusted claims and absence costs by the risk score.

The benefit of having an individual not in the program join it is then determined as follows: (1) the individual's medical and pharmacy claims, and medically-related absence costs, for the current year, multiplied by (2) the program's average risk-adjusted percentage decrease in costs, less (3) the cost of the program.

For example, Employee C is identified as an individual with diabetes who is not participating in the diabetes program. Employee C's current year medical and pharmacy costs are $7,000, and their current year absence costs related to those claims are $2,000. The average percentage decrease in risk-adjusted costs for participants in the program is 22%, and the vendor charges $700 per participant. The potential benefit of getting Employee C to participate is $1,280, calculated as follows: (($7,000+$2,000)×22%)−$700=$1,280.

The engine can recommend wellness programs to implement and determine their likely impact on the health plan's medical and pharmacy claims and medically-related absence costs. Similarly, the engine can recommend safety programs to implement under the workers' compensation program to address job-related injuries and the likely impact of such safety programs on the workers' compensation program's costs.

To do so the engine identifies potential programs by comparing the list of root diagnoses in the health plan medical and pharmacy claims against the list of implemented programs to identify diagnoses without an associated program (and similarly compares the injuries in the workers' compensation claims to the list of implemented safety programs).

The engine determines the likely per person percentage benefit of a potential program in terms of decreased medical and pharmacy claims and medically-related absence costs, as well as the cost of the program, from publicly available information and program vendor materials. The engine may augment this determination by employing artificial intelligence and machine learning techniques concerning the impact of such a program on similar demographic populations by using patient predictor variables such as personal and job demographics, risk scores, SDOH, health plan/clinical data, and comorbidities.

The engine determines each potential program's likely healthcare outcome/overall ROI if patients with the root diagnosis that the program addresses participated in the program by taking (1) the value of the medical and pharmacy claims, and medically-related absence costs, for the current year of each such patient, (2) multiplying such claims and absence costs by the program's likely per person percentage benefit, (3) aggregating such amounts for all such patients (or a selected percentage of them), subtracting (4) the program's likely cost for such patients, and dividing that difference by (5) the program's likely cost for such patients.

The engine recommends the adoption of any program not currently implemented for which the ROI equals or exceeds a threshold ROI selected by the user.

For example, assume that the navigation engine identifies 500 patients on an employer's health plan with diabetes, but the employer does not have a diabetes disease management program. Based on an analysis of publicly available information and diabetes program vendor materials, coupled artificial intelligence and machine learning techniques employed upon the population health and demographics of these 500 patients, the engine determines that the likely per person percentage benefit of a potential diabetes program is 11%. The average value of the medical and pharmacy claims and medically-related absence costs for these 500 patients is currently $10,500, and a program vendor will charge $1,000 per participant. The likely ROI for a diabetes program would be 15.5%, calculated as follows: (($10,500×500×11%)−($1,000×500))÷($1,000×500)=15.5%. If the user has set the threshold for recommending a program at 12.5%, the engine would recommend that the employer adopt this program.

This detailed description does not limit or represent an exhaustive enumeration of the disclosed principles. It will be apparent to those of skill in the art that numerous changes may be made in such details without departing from the spirit of the disclosed principles, and that the navigation engine does not require all the features described above to be deployed for the engine to function.

We claim:

1. A method and/or system of navigating through, and searching in, a computing environment (i.e., the navigation engine) to evaluate wellness programs on a quantitative basis based on their impact on the participants' healthcare costs and absences from work, and which then determines the ROIs (Returns on Investment) on such programs, comprising:

presenting a system of visual navigation on a single computer screen for an individual (i.e., the user) using the computer along with a monitor and mouse, that represents categories and subcategories (and sub-subcategories, etc.) of material with functionally labeled circles or other images in a hierarchical organization;

organizing that order with a central circle branching off into several smaller circles connected by stems, and from each of those smaller circles several more even smaller circles so connected, with more detailed subsets of the material as the circles descend;

displaying thumbnails of the dashboards and reports available under a circle when the user hovers the computer mouse's cursor over it;

accessing those dashboards and reports when the user clicks the mouse's cursor over the circle, or alternatively opening a particular dashboard or report directly when the user clicks on its thumbnail;

linking the color of each circle for a wellness program to the navigation engine's determination of the program's ROI, which may include shading such color darker or lighter based on where the ROI falls within the color's range;

organizing employer human resources (HR) data (e.g., time & attendance, payroll, turnover, etc.) and wellness program data (e.g., enrollment and cost) in databases arranged in tables with schemas that permit the engine to extract the data and perform the engine's algorithms on it;

determining the number of sick or PTO (Paid Time Off) days (i.e., absence days) for each employee participating in the program during that employee's base year (i.e., the year immediately before the employee joined the program);

constructing a synthetic base year of the number of absence days for each employee that joined the program in the first year that the employee became an employee based on the average base year absence days of similarly situated employees as determined using the HR data set (e.g., age, gender, job description, location, and other job demographics);

comparing the base year absence days to the current year absence days (or other period under evaluation) for each employee participating in the program;

valuing the excess of the base year absence days over the current year absence days at the employee's current year compensation rate or a normalized rate for all employees (which will be a positive number if the base year days exceed the current year days, and a negative number if the current year days exceed the base year days);

aggregating these values for all the employees participating in the program to determine the program's occupational outcome for the current year or other period under evaluation;

determining the program's occupational outcome ROI for the current year (or other period under evaluation) by taking (1) the overall value of the change in absence days (may be positive or negative), less (2) the overall cost of the program (if the overall value of the change in absence days is positive, this will decrease that positive value, while if the overall change is negative it will increase it), and then dividing that difference by (3) the overall cost of the program;

determining the program's occupational outcome ROI since the inception of the program by taking (1) the aggregate of the overall value of the change in absence days for each year of the program, increased for inflation (or decreased for deflation) from such year to the current year, less (2) the aggregate of the overall cost of the program during each year, increased for inflation (or decreased for deflation) from such year to the current year, and then dividing that difference by (3) the aggregate of the overall cost of the program during each year, increased for inflation (or decreased for deflation) from such year to the current year; and filtering the results by various metrics and/or combinations thereof, including programs, periods, business units and/or departments, job descriptions and/or functions, and employer locations and/or geographies.

2. The method and/or system of claim 1, as well as comprising:

assigning a change in absence day value of zero (or a selected negative amount based on the employer's turnover costs) to an employee participating in a wellness program that is an EAP (Employee Assistance Program) when the employee terminates their employment, voluntarily or involuntarily, during the current year (or other period under evaluation).

3. The method and/or system of claim 1, as well as comprising:

organizing the medical and pharmacy claims under a health plan and/or workers' compensation program in databases arranged in tables with schemas that permit the engine to extract the data and perform the engine's algorithms on it;

grouping the claims for the base year and the current year (or other period under evaluation) of each individual in the claims data set (i.e., the patient) according to the root diagnosis (i.e., the condition or injury causing the claim) based upon the diagnosis, procedure and other codes in the claims;

juxtaposing the dates of the claims for each root diagnosis against the employer's sick or PTO days for each patient who is an employee to identify the absence days related to those claims, and then valuing such medically-related absences at the employee's compensation rate during the respective year (or a normalized rate for all the employees during that year);

analyzing each patient's age, gender and medical and pharmacy claims, independently or in combination with the patient's social determinants of health (SDOH), job demographics and/or health plan/clinical data, to assign the patient a risk score indicating the patient's health, with a score of 1.000 assigned to a patient of average health, below 1.000 to a patient healthier than average (the lower the score, the healthier), and above 1.000 to a patient sicker than average (the higher the score, the sicker);

constructing a synthetic base year of the claims and medically-related absence days for each patient joining the wellness program in the first year that the patient joined the health plan and/or employer based on the patient's risk score, medical and pharmacy claims, and medically-related absence costs contained in the individual's first year of data as compared to the base years of similar individuals participating in the program;

adjusting the value of the claims and medically-related absence costs for inflation/deflation to the current year for each patient's base year or synthetic base year (and any years after the base year, but before the current year);

selecting the claims (and by implication the medically-related absence costs) to use when evaluating the wellness program: (1) for a general wellness program (e.g., walking or weight watchers) the user may select all medical and pharmacy claims and medically-related absence costs, or only those concerning chronic conditions, (2) for a disease management program (e.g., diabetes or obesity) the user may select all medical and pharmacy claims and medically-related absence costs, only those concerning chronic conditions (including behavioral health issues), or only those concerning the specific chronic condition that the program addresses, and (3) for EAPs (i.e., programs addressing behavioral health issues) the user may select all medical and pharmacy claims and medically-related absence costs, only those concerning chronic conditions (including behavioral health issues), only those concerning behavioral health issues, or only those concerning the specific behavioral health issue that the program addresses;

comparing the value of the base year claims and medically-related absences (adjusted for inflation/deflation to the current year) to the value of the current year claims and medically-related absences (or other period under evaluation) for each participant in the program (which will be a positive number if the base year value exceeds the current year value, and a negative number if the current year value exceeds the base year value);

aggregating these values for all the participants in the program to determine the program's healthcare outcome for the current year or other period under evaluation;

determining the program's healthcare outcome/overall ROI for the current year (or other period under evaluation) by taking (1) the overall value of the change in claims and medically-related absences (may be positive or negative, a positive number when these costs have decreased, and a negative number when they have increased), less (2) the overall cost of the program (if the overall value of the change in claims and medically-related absences is positive, this will decrease that positive value, while if the overall change is negative it will increase it), and then dividing that difference by (3) the overall cost of the program;

determining the program's healthcare outcome/overall ROI since the inception of the program by taking (1) the aggregate of the overall value of the change in claims and medically-related absences for each year of the program, adjusted for inflation/deflation from such year to the current year, less (2) the aggregate of the overall cost of the program during each year, adjusted for inflation/deflation from such year to the current year, and then dividing that difference by (3) the aggregate of the overall cost of the program during each year, adjusted for inflation/deflation from such year to the current year; and filtering the results by additional metrics and/or combinations thereof, including employees versus dependents, risk scores, SDOH, job demographics and health plan/clinical data, including the type of health plan covering the person.

4. The method and/or system of claim 3, as well as comprising:

including in the ROI determination for an EAP a savings component based on the decrease in the number of participants terminating their employment (voluntarily or involuntarily) during the current year (or other year under evaluation) compared to the anticipated number based on the termination rate in the program's base year for employees with the respective behavioral health issue, valued at the employer's turnover cost per employee.

5. The method and/or system of claim 4, as well as comprising:

mapping the list of root diagnoses identified in the medical and pharmacy claims to the disease management programs and EAPs that address those conditions;

cataloging the root diagnoses in each patient's medical and pharmacy claims;

comparing each patient's root diagnoses to the enrollment of the disease management programs and EAPs to identify patients not participating in a program who could benefit from it;

determining the average risk-adjusted per person percentage benefit of each program by taking: (1) the average base year risk-adjusted medical and pharmacy claims, and medically-related absence costs, adjusted for inflation/deflation, of the participants in the program, less (2) their average current year risk-adjusted claims and absence costs, and dividing that difference by (3) their average base year risk-adjusted claims and absence costs adjusted for inflation/deflation (when making this determination, any participant with a risk score below 1.000 is assigned a risk score of 1.000, and the average risk-adjusted claims and absence costs are determined by dividing the unadjusted claims and absence costs by the risk score); and determining the impact on the program's healthcare outcome/overall ROI if patients not participating in the program, but who could benefit from it, participated by taking (1) the medical and pharmacy claims, and medically-related absence costs, for the current year of each such patient, (2) multiplying such claims and absence costs by the program's average risk-adjusted per person percentage benefit, (3) aggregating such amounts for all such patients (or a selected percentage of them), subtracting (4) the program's cost for such patients, and dividing that difference by (5) the program's cost for such patients.

6. The method and/or system of claim 5, as well as comprising:

determining the wellness programs not implemented that should be considered by comparing the list of root diagnoses in the health plan medical and pharmacy claims against the list of implemented programs to identify root diagnoses without an associated program (and similarly comparing the injuries in the workers' compensation claims to the list of implemented safety programs);

determining the likely per person percentage benefits of such potential programs in terms of decreased medical and pharmacy claims and medically-related absence costs, as well as the cost of the potential programs, from publicly available information and program vendor materials (which determination may be augmented by employing artificial intelligence and machine learning techniques concerning the impact of such programs on similar demographic populations by using patient predictor variables such as personal and job demographics, risk scores, SDOH, health plan/clinical data, and comorbidities);

determining each such potential program's likely healthcare outcome/overall ROI if patients with the root diagnosis that the program addresses participated in the program by taking (1) the value of the medical and pharmacy claims, and medically-related absence costs, for the current year of each such patient, (2) multiplying such claims and absence costs by the program's likely per person percentage benefit, (3) aggregating such amounts for all such patients (or a selected percentage of them), subtracting (4) the program's likely cost for such patients, and dividing that difference by (5) the program's likely cost for such patients; and recommending the adoption of any potential program for which the ROI equals or exceeds a threshold ROI selected by the user.

* * * * *